United States Patent [19]

Shimizu et al.

[11] Patent Number: 5,310,728
[45] Date of Patent: May 10, 1994

[54] METHOD FOR TREATING CORNEAL ENDOTHELIAL WOUNDS

[75] Inventors: Robert W. Shimizu, Irvine, Calif.; Gregory S. Schultz, Gainesville, Fla.

[73] Assignee: Chiron Ophthalmics, Inc., Irvine, Calif.

[21] Appl. No.: 918,808

[22] Filed: Jul. 23, 1992

Related U.S. Application Data

[63] Continuation of Ser. No. 562,003, Aug. 1, 1990, abandoned.

[51] Int. Cl.$^5$ ............................................. A61K 37/36
[52] U.S. Cl. ................................. 514/12; 514/23; 514/912; 514/961; 514/970; 424/78.04
[58] Field of Search ............ 514/12, 23, 912, 961, 514/970; 424/78

[56] References Cited

U.S. PATENT DOCUMENTS

| | | | |
|---|---|---|---|
| 4,713,446 | 12/1987 | DeVore et al. | 530/356 |
| 4,929,442 | 5/1990 | Powell | 424/85.2 |
| 4,939,135 | 7/1990 | Robertson | 514/179 |

FOREIGN PATENT DOCUMENTS

0190018A2  8/1986  European Pat. Off. .

OTHER PUBLICATIONS

Pape, L. G. et al., Am. Intra-Ocular Implant Soc. J., vol. 6, p. 342 (1980).
DeLarco et al., Proc. Natl Acad. Sci., vol. 75:4001 (1978).
Marquardt et al., Science, 223:1079 (1984).
Schultz, G. S., et al. Science, 235:350 (1987).
Cifone et al., Proc. Natl Acad. Sci. USA 77:1039 (1980).
Haigler & Carpenter, Biochem. Biophys. Acta 598:314 (1980).
Rich et al., *The Influence of Fibroblast Growth Factor on Healing of Cat Corneal Endothelium*, ARVO 1989, Invest. Ophthal. Vis. Sci., 30(3).

*Primary Examiner*—F. T. Moezie
*Attorney, Agent, or Firm*—Rothwell, Figg, Ernst & Kurz

[57] ABSTRACT

A method for treating corneal endothelial wounds comprises administering TGF-α to the region of the wound in an amount sufficient to promote the healing of endothelial cells.

TGF-α advantageously is administered into the anterior chamber during ophthalmic surgical procedures, such as during intra-ocular lens implantation. The TGF-α preferably is administered as an active ingredient in an ophthalmological viscoelastic composition which improves the residence time of the growth factor in the anterior chamber.

7 Claims, 6 Drawing Sheets

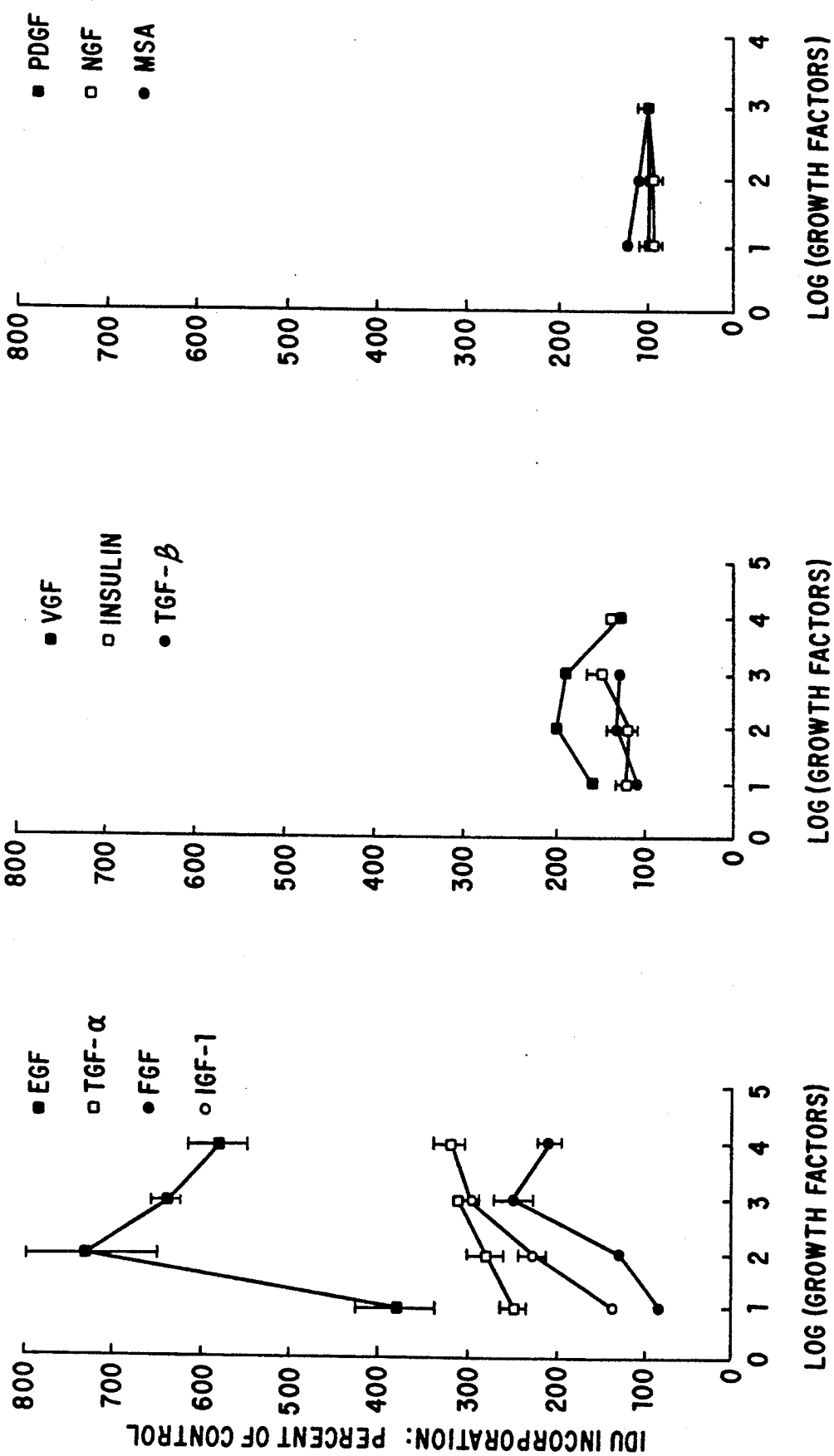

METHOD FOR TREATING CORNEAL ENDOTHELIAL WOUNDS

This is a continuation of application Ser. No. 07/562,003, filed Aug. 1, 1990 now abandoned.

FIELD OF THE INVENTION

This invention relates to a method for treating corneal endothelial wounds. More specifically, this invention relates to a method of promoting the healing of endothelial cells subject to injury, disease or ophthalmic surgery by administering to the region of the wound transforming growth factor alpha to promote the healing of such cells.

BACKGROUND OF THE INVENTION

The cornea is made of a series of layers. In humans, the anterior layer, known as the epithelium, serves the function of maintaining the integrity of the cornea. Components of epithelial cells regulate the transport of fluids and electrolytes through lamellae of the stroma, which is separated from the epithelium by a thin layer known as the Bowman's membrane. Beneath the stroma is another layer, Descemet's membrane, which separates the stroma from the endothelium, a thin layer of cells forming the posterior surface of the cornea.

Between the endothelial layer of the cornea and the lens of the eye is the anterior chamber. The anterior chamber contains fluid, known as the aqueous humor, which is produced by the eye.

The cornea and lens of the eye can be subject to trauma as a result of disease, injury to, or surgery on the eye. Given the delicate nature of the eye, it is important to have the rate of healing from such traumas be as rapid as possible and to minimize undesirable effects associated with natural wound-healing processes, such as scarring and contraction of healed tissues. Such effects can interfere with visual function.

One of the dangers of any trauma to the eye is damage to the endothelium. Endothelial cells in adults mitose only rarely, and the population of endothelial cells generally decreases with age; thus, it is important that damage to these cells be minimized and healing be enhanced.

There have been a number of advances in ophthalmic surgery in recent years which have provided great benefits but which also have increased the risk of damage to or destruction of endothelial cells during the surgical procedures. For example, intraocular lens (IOL) implantation and corneal transplantation can result in damage to endothelial cells. The risk to the cells can be great, for simply having the cells come into contact with, for example, surgical instruments, can result in what is known as a "touch injury."

A number of efforts have been made to find ways to protect endothelial cells during or following surgical procedures. For example, U.S. Pat. No. 4,713,446, issued to DeVore et al. (1987), describes injecting viscoelastic collagen solutions into the anterior chamber of the eye to maintain anterior chamber depth during surgery. If the depth of the chamber cannot be maintained, the cornea can collapse toward the lens, increasing the risk that the endothelium will suffer a touch injury. The viscoelastic materials help to protect cell surfaces from mechanical trauma and create space by keeping adjacent but not adherent tissue surfaces separated during surgical procedures. The use of other viscoelastic compositions also have been described. See, for example, Pape, L. G. et al., *Am. Acad. Ophthal.*, 87(7):699 (1980), which describes the use of viscoelastic compositions of hyaluronic acid in a variety of anterior segment surgical procedures.

Although the viscoelastic compositions described in these and other references have proven to be useful, further methods are desired to help protect endothelial cells and enhance wound healing.

SUMMARY OF THE INVENTION

In accordance with the present invention, a method for enhancing the healing of wounds of the corneal endothelium comprises administering transforming growth factor alpha to the region of the endothelium to promote healing of the endothelial cells. The TGF-α appears to promote healing by stimulating mitosis of the endothelial cells. The TGF-α can be administered in the form of an ophthalmological viscoelastic composition, irrigating solution or an injectable solution. Viscoelastic compositions presently are preferred.

BRIEF DESCRIPTION OF THE FIGURES

FIG. 5 is a series of three graphs showing the stimulation of DNA synthesis by certain growth factors.

DETAILED DESCRIPTION OF THE INVENTION

Figure 1:
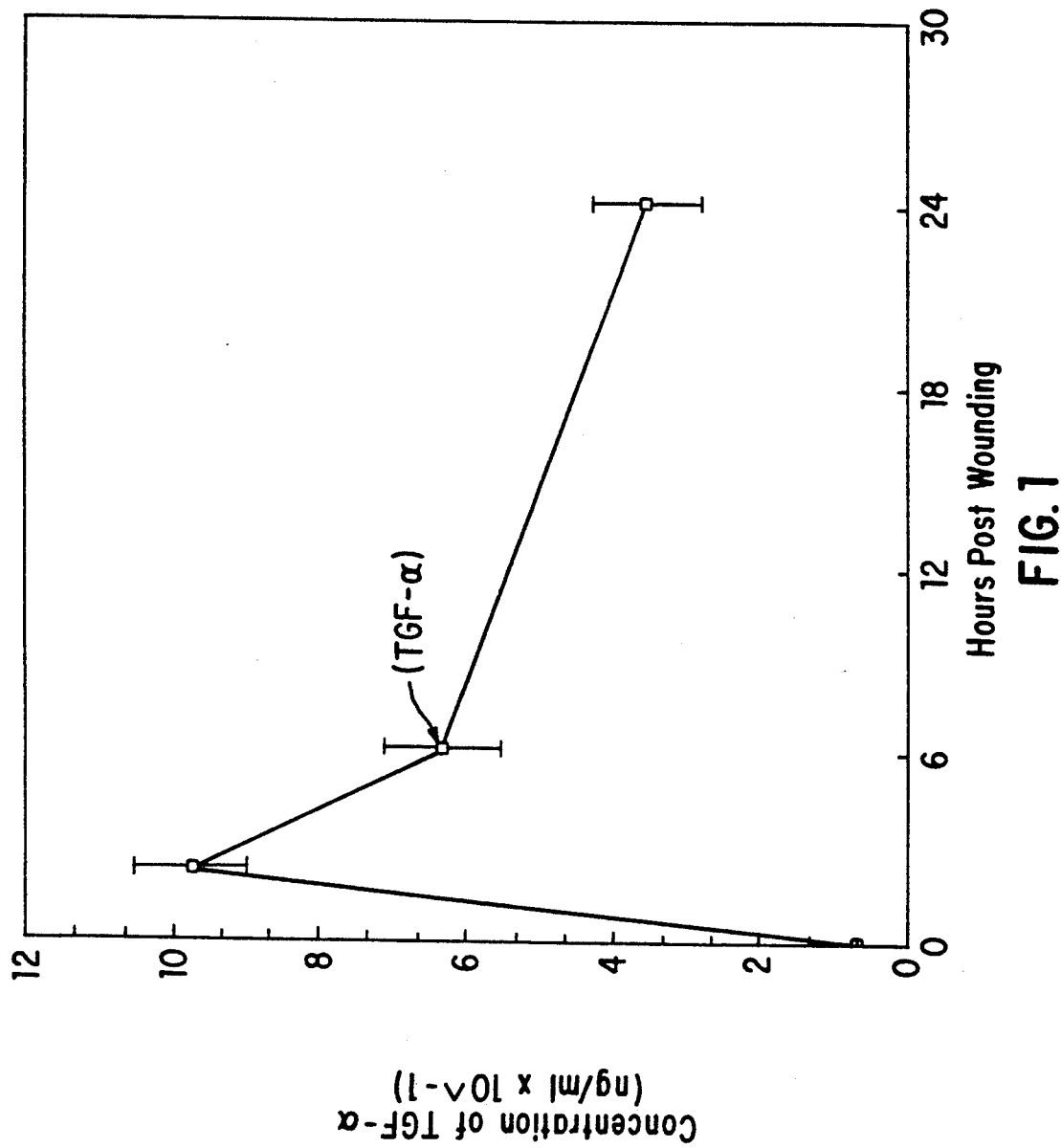
FIG. 1 is a graph showing the relative concentrations of TGF-α in the fluid of the anterior chamber of the eye prior to and following wounding of the corneal epithelium.

Growth factors are polypeptides which cause cells to migrate, differentiate, transform and divide. These polypeptides can be isolated from various mammalian cell types, and some of them also can be produced by genetically engineered microorganisms and by solid phase peptide synthesis. One growth factor is transforming growth factor alpha (hereinafter referred to as TGF-α), a single polypeptide having a molecular weight of approximately 5600. The polypeptide is secreted by transformed mammalian cells in culture as described by DeLarco et al., *Proc. Nat. Acad. Sci.*, vol. 75:4001 (1978). The amino acid sequence has been reported by Marquardt et al., *Science*, 223:1079 (1984). TGF-α is known to stimulate DNA synthesis and growth of cells in culture, apparently by binding to specific receptors in cell membranes which also bind epidermal growth factor (EGF), a growth factor which is structurally related to TGF-α and also plays a role in regulating the growth of mammalian cells. Although TGF-α and EGF are similar in many regards, researchers also have demonstrated that there are some significant differences in their biological responses and in the biochemical manner in which they bind to the receptor. These differences can make it difficult to predict accurately the relative effects of the factors on target tissues.

It is known that TGF-α can be topically applied to wounds, such as burns, to accelerate epidermal regeneration. See Schultz, G. S. et al., *Science*, 235:350 (1987).

It also has been reported that the polypeptide can be topically applied to cancerous or virus-caused skin disorders in combination with an antiviral surfactant, human interferon and an adjuvant to aid in treating such skin disorders. See U.S. Pat. No. 4,929,442, issued to Powell (1990).

It now has been discovered that TGF-α also plays a role in the healing of endothelial cells. It has been discovered that TGF-α plays a role in the normal physiological response of the anterior chamber of the eye to trauma. It has been found that TGF-α is a potent mitogen for pure cultures of bovine corneal endothelial cells and that the level of TGF-α present in the aqueous humor in the anterior chamber increases significantly following physical injury to the corneal endothelium and then remains higher than pre-injury levels for twenty four hours. When samples of such TGF-α-enriched aqueous humor are added to cultures of endothelial cells, an enhanced level of mitogenic activity is observed (see example 2, below). In addition, a significant reduction in mitotic activity of anterior chamber fluids occurs when a specific antibody is added that neutralize TGF-α.

In accordance with the present invention, a method for enhancing the healing of wounds to the corneal endothelium comprises administering TGF-α to the region of the wound in amounts sufficient to promote healing of the endothelial cells. It appears that the TGF-α promotes healing by stimulating mitosis of the endothelial cells. As used herein, "wound" refers to surgical incisions as well as wounds caused by accidental trauma or disease.

Also as used herein, TGF-α refers to a polypeptide having an amino acid sequence and biological activity, particularly the mitogenic activity, of full-length, natural TGF-α as measured by recognized bioassays, such as those described by Cifone et al., *Proc. Nat. Acad. Sci. USA* 77:1039 (1980), and DeLarco et al., *Proc. Nat. Acad. Sci. USA* 75:4001 (1978). The term refers to natural, synthetic or recombinant TGF-α or biologically active fragments or analogs thereof. Full-length TGF-α is available commercially from Triton Biosciences, Inc., Alameda, Calif.

The invention will be described in further detail with specific reference to its application in intraocular lens implantation. It will be understood, however, that the invention can be applied at any time the cornea of the eye is wounded and endothelial cells have been, or are at risk of being, damaged.

As has been noted above, viscoelastic compositions can be administered to the anterior chamber of the eye during an IOL implantation procedure to lessen the risk of endothelial-IOL contact and significant corneal endothelial damage. Suitable compositions include buffered physiologically acceptable solutions of about 0.1% to about 3.0% by weight sodium hyaluronate, such as Healon ™ (Pharmacia Co., Inc., Piscataway, N.J.), about 0.1% to about 5.0% by weight collagen, such as Collagel ™ (manufactured by Biodomi, Lyon, France), or about 0.1% to about 5.0% by weight chondroitin sulfate, such as Viscoat ™, Alcon ™ and Occugel (all made by Surgidev, Corp., Galeta, Calif.). Other suitable compositions include ophthalmic compositions of about 1.0% to about 10% by weight polyacrylamide, such as Orcolon ™ (Optical Radiation Corp., Azusa, Calif.) or about 1% to about 5.0% by weight hydroxypropylmethylcellulose, such as Occucoat ™ or Occugel (made by Storz Ophthalmics Inc., Clearwater, Fla., and Surgidev Corp., Galeta, Calif., respectively). In accordance with this invention, TGF-α is added to such compositions in concentrations sufficient to enhance endothelial cell healing. Typically, the TGF-α is added to the compositions in concentrations ranging from about 1 µg/ml to about 100 µg/ml. Preferably, the TGF-α concentration is about 30 µg/ml to about 100 µg/ml.

The TGF desirably is added during the formation of the viscoelastic material. For example, a sterile concentrated solution (e.g., 10 to 100 times the desired final concentration) of TGF-α is made in a desired vehicle, such as saline or phosphate buffer. The concentrated solution then is mixed aseptically to homogeneity with the viscoelastic polymer solution. The solution then is packaged in sterile containers aseptically.

Viscoelastic compositions containing TGF-α can be administered intracamerally to fill the anterior chamber at the beginning of the surgical procedure. The surgical maneuvers then are carried out under the protection of the viscoelastic material in accordance with recognized practices. At the conclusion of the surgery additional viscoelastic material can be added to the anterior chamber both to retain space between the endothelium and the lens for a desired period of time and to maximize the time of contact between the exogenous TGF-α and the endothelial cells.

Desirably, the viscoelastic material is administered such that at least a physiologically active amount of TGF-α, typically about 50 µg, is provided to the anterior chamber at or near the beginning of the surgical procedure to provide both a sufficient level and a sufficient time of exposure to stimulate cell division. In general, peptide growth factors require prolonged continuous exposure to cells to stimulate mitosis. For example, EGF requires a minimum of about 6 hours to induce fibroblasts to divide *in vitro*. See Haigler & Carpenter, *Biochim. Biophys. Acta* 598:314 (1980).

In addition to injecting the viscoelastic material containing the TGF-α directly into the anterior chamber, it also can be desirable to coat the intra-ocular lens and the surgical implements with the material to provide a further degree of endothelial protection.

As noted above, in addition to the use of viscoelastic materials, the TGF-α can be administered in the form of an ophthalmological irrigating solution or an injectable solution. Suitable irrigating solutions include those comprising ions (sodium, potassium, calcium, magnesium, chloride, phosphate, bicarbonate, acetate, citrate and lactate), glucose and glutathione and sold, for example, under the names BBS and BBS Plus. Typically, the TGF-α is added to such solutions to provide concentrations ranging from about 10 ng/ml to about 1 mg/ml, and preferably concentrations ranging from about 10 µg/ml to about 100 µg/ml. The solutions then can be used to wash the eye, specifically, the endothelium, at periodic intervals throughout the surgical procedure. Some of the solution can be left in the anterior chamber at the conclusion of the surgical procedure to provide additional time for the TGF-α to be in contact with the endothelial cells.

In an alternative embodiment, it is contemplated that the TGF-α could be added to a solution that could be injected directly into the anterior chamber. For example, it is contemplated that a series of injections could be administered to certain patients who have suffered a minimal amount of damage to their endothelium as a means of healing the endothelium without having to resort to surgery. The TGF-α could be added to such solutions to provide concentrations ranging from about 0.1 μg/ml to about 100 μg/ml.

To make either an irrigating solution or an injectable solution, the TGF-α could be provided either as a ready made solution or as a lyophilized cake. If a lyophilized cake is used, the TGF-α could be dissolved in the desired vehicle at the time of use. In general, albumin often is provided in such lyophilized cakes to help stabilize the polypeptide during processing.

The invention is further illustrated by the following examples, which are provided for the purposes of illustration and are not intended to be limiting.

EXAMPLE 1

Detection of TGF-α in the Aqueous Humor Following a Touch Injury

Nine cats were anesthetized with Ketamine/Rompum in accordance with conventional procedures. An anterior chamber cannula connected to a reservoir of physiological saline was inserted into the anterior chamber of both eyes of each cat, then the reservoirs were opened. Samples of anterior chamber fluid was obtained from each eye of all cats prior to making the injury. Then, a 7 mm trephine impression was made to the corneal surface, a stab incision was made at the limbus by Super blade and a diamond dusted capsule polisher was inserted through the stab incision and used to sweep the endothelium in the area of the trephine impression. Both eyes of all cats were operated. Following the injury, the cannulas were removed and the eyes were allowed to reform without placement of sutures.

The cats were divided into three groups of three cats each. At 2, 6 and 24 hours after the touch injury was made, anterior chamber fluid was removed from each eye of each cat and stored at 4° C. until analyzed.

The samples were assayed for TGF-α immunoreactivity using a commercially available radioimmunoassay for TGF-α supplied from Biotop, Inc., Seattle, Wash. Each sample was assayed in duplicate at three dilutions following reduction and denaturation according to manufacturer's instructions. The TGF-α RIA is specific for TGF-α and does not recognize EGF or related molecules of similar size.

Calculation of the relative mean concentrations of TGF-α in the samples generated the curve shown in FIG. 1. It is apparent from the curve that low levels of TGF-α were present in the anterior chamber fluid immediately prior to wounding. Two hours after the wounding, the concentration had increased approximately 16 fold. The concentrations had dropped by 6 and 24 hours after the wounding; the level was approximately 6 fold higher than the pre-injury level 24 hours after surgery. The mean and standard error of the means for the samples are shown in Table 1.

TABLE 1

| Concentrations of TGF-α In Anterior Chamber Samples | | | |
|---|---|---|---|
| Sample | Mean (ng/ml) | SEM | Number of Samples |
| 0 hr | 6.83 | 1.06 | 18 |
| 2 hr | 97.44 | 7.84 | 5 |
| 6 hr | 63.28 | 7.84 | 6 |
| 24 hr | 35.46 | 7.28 | 6 |

A statistical analysis of the average concentrations for the samples is shown in Table 2.

TABLE 2

| Statistical Analysis of TGF-α Levels from Anterior Chamber Samples | | | |
|---|---|---|---|
| Samples | t | p | df |
| 0 hr vs 2 hr | −29.105 | $1.1 \times 10^{-16}$ | 21 |
| 0 hr v 6 hr | −17.675 | $1.72 \times 10^{-14}$ | 22 |
| 0 hr vs 24 hr | −9.715 | $2.036 \times 10^{-9}$ | 9 |
| 2 hr vs 6 hr | 4.688 | $2.724 \times 10^{-3}$ | 9 |
| 2 hr vs 24 hr | 7.837 | $2.606 \times 10^{-5}$ | 9 |
| 6 hr vs 24 hr | 3.664 | $4.359 \times 10^{-3}$ | 10 |

The concentrations for each sample is significantly different from all other samples by probability values of $p < 0.05$.

Figure 2A:
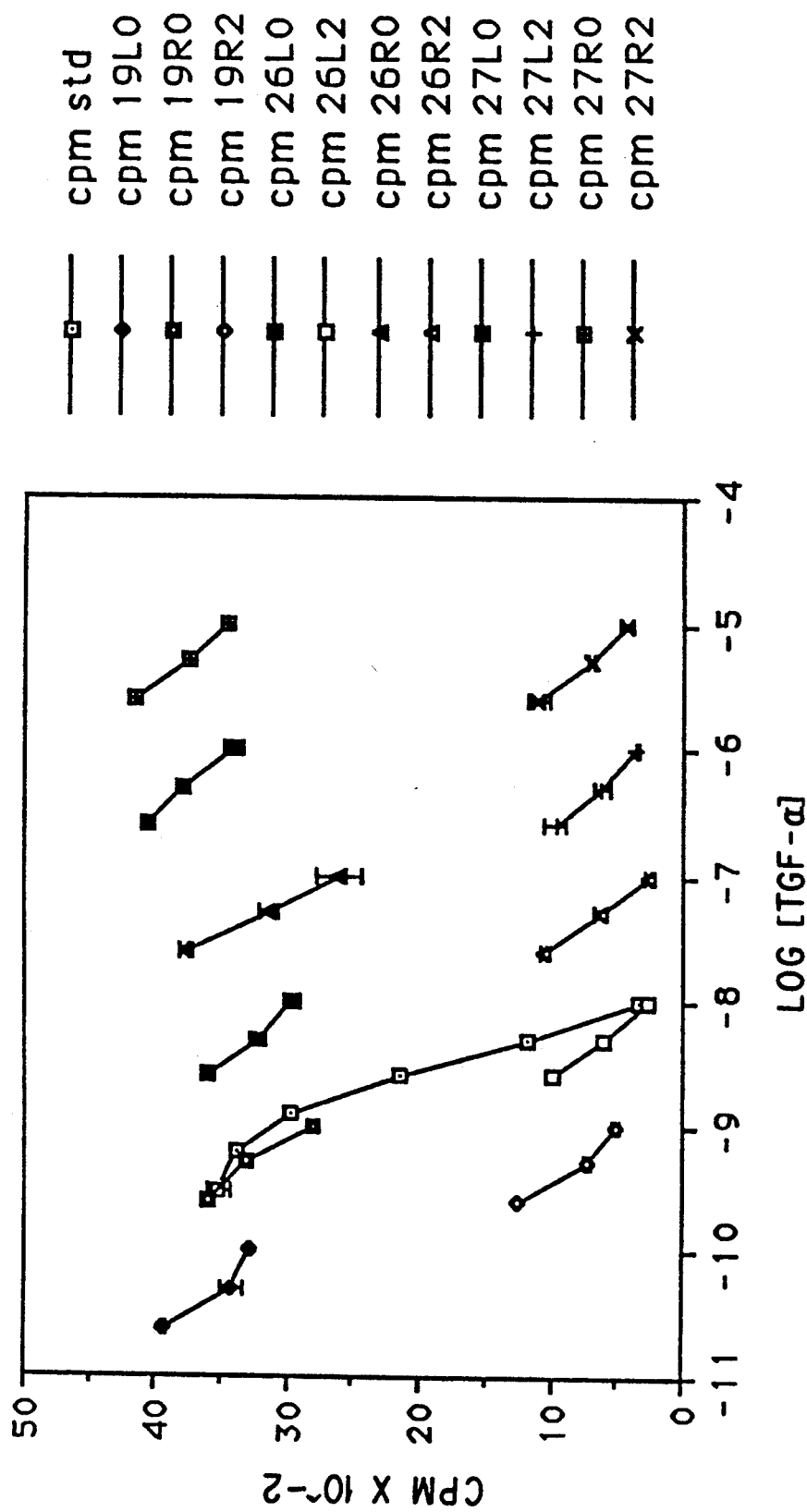
FIG. 2 is a displacement curve for samples of anterior chamber fluid taken 2 hours following corneal epithelium wounding.
Figure 2B:
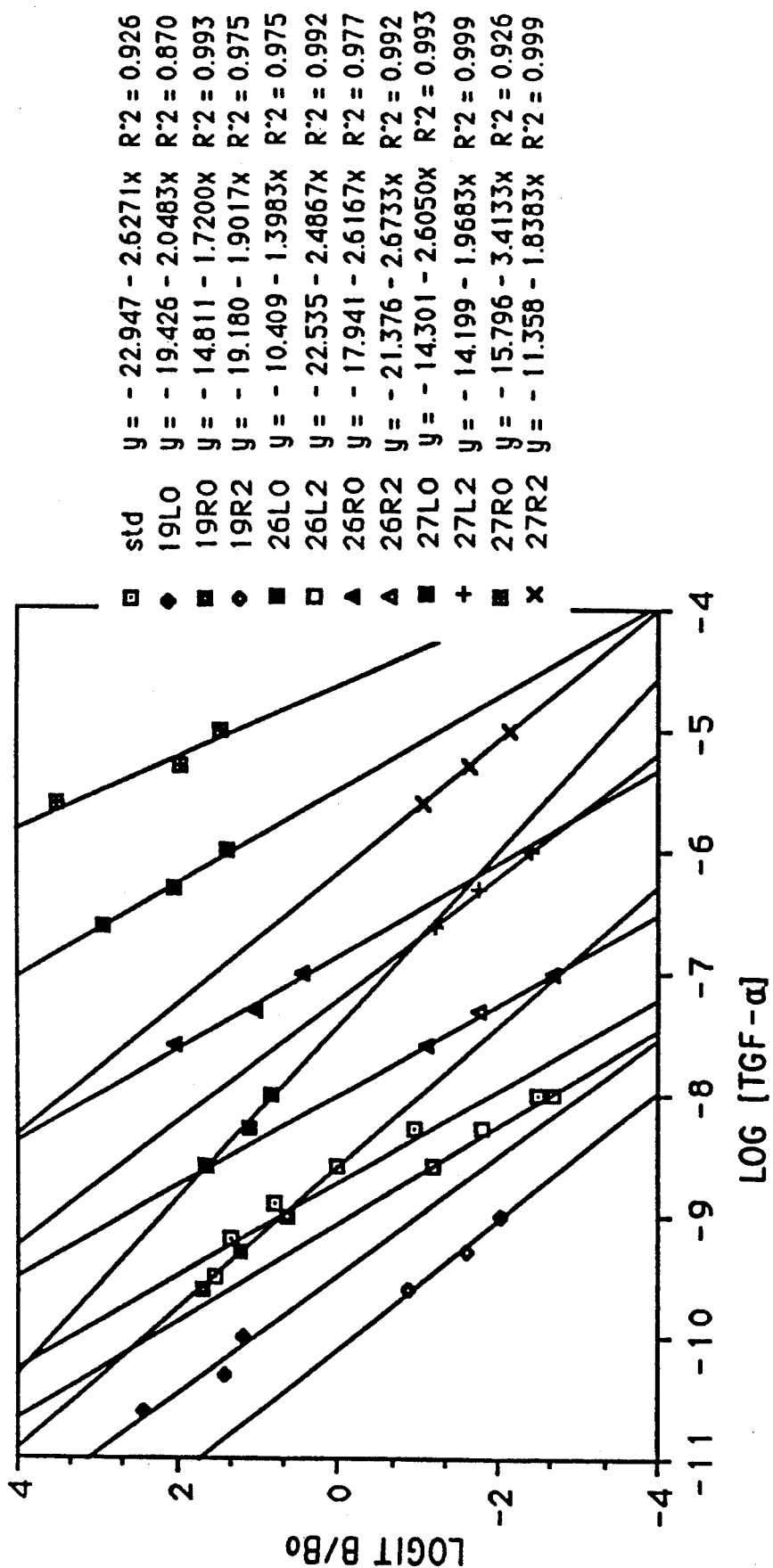

The displacement curves for the 2 hour samples are shown in FIG. 2. The curves were similar for the 0, 6 and 24 hour samples. In the legend accompanying the figures, the numbers 19, 26 and 27 represent the test group, L and R stand for left or right eye fluid, respectively, and 0 and 2 represent zero time and two hours post-wounding, respectively.

Transformation of the displacement curves by logit transformation demonstrated parallel slopes of the TGF-α standard and anterior chamber samples. Parallel displacement is an essential criterion in establishing that the displacement produced by the anterior chamber samples is due to TGF-α and not to nonspecific displacement. Parallel slopes also were shown for the 6 and 24 hour post-wounding samples.

EXAMPLE 2

Determination of Biological Activity of Immunoreactive TGF-α Material

The study described in Example 1 showed that anterior chamber fluid from cats following touch injuries to the endothelium contained substantial levels of immunoreactive TGF-α material. The following experiment was performed to determine whether the immunoreactive material also could have biological activity. The target cells chosen for the study were early passage cultures of bovine corneal endothelial cells (BCEC) known to respond mitogenically to TGF-α.

The solutions of anterior chamber fluids obtained in Example 1, above, were the test samples in this study. Early passage cultures of BCEC were trypsinized and seeded in 24 well culture plates at approximately 50 percent confluency. The BCEC were cultured for 48 hours in a chemically defined medium (CDM) composed of equal parts of Medium 199, Dulbecco's modified Eagle's medium, and Ham's F-12 supplemented with 10% newborn calf serum. The cells were washed with CDM lacking serum for 24 hours to synchronize the cells by serum deprivation. After the serum free medium was removed, each well received 200 μl of CDM containing tritiated thymidine at 5 μCi per well. Six different test conditions were evaluated with each condition containing four replicate wells for a total of 24 assay wells. The test conditions were 0% calf serum, 10% calf serum, 0 hour, 2 hours, 6 hours and 24 hours samples of anterior chamber fluid. Each of the anterior chamber fluid samples was filter sterilized through 0.22 μ pore nylon filter prior to introduction into the assay system. The cells were incubated for 48 hours, then incubation medium was removed by aspiration and the plate was submerged in a solution of 10% trichloroacetic acid and then in methanol. The plate was allowed to air dry and 1 ml of 0.1N sodium hydroxide was added to dissolve the cell contents, including the DNA. Nine hundred μl of the dissolved cell solution was added to a liquid scintillation cocktail and counted by beta scintillation counting.

The results of the DNA stimulation assay are shown in Table 3.

TABLE 3

Tritiated Thymidine Incorporation Into DNA or Bovine Corneal Endothelial Cells In Vitro By Cat Anterior Chamber Fluid Samples

| Sample | Well | CPM | Mean | SD | SEM |
| --- | --- | --- | --- | --- | --- |
| CDM | 1 | 387,713 | 474,941 | 58,823 | 26,306 |
|  | 2 | 413,013 |  |  |  |
|  | 3 | 542,282 |  |  |  |
|  | 4 | 472,285 |  |  |  |
|  | 5 | 459,419 |  |  |  |
| 10% Serum | 6 | 1,742,340 | 1,487,000 | 404,998 | 202,499 |
|  | 7 | 1,668,759 |  |  |  |
|  | 8 | 882,538 |  |  |  |
|  | 9 | 1,655,704 |  |  |  |
| 0 hr | 10 | 1,542,447 | 1,344,507 | 440,283 | 220,141 |
|  | 11 | 684,689 |  |  |  |
|  | 12 | 1,588,516 |  |  |  |
|  | 13 | 1,562,373 |  |  |  |
| 2 hr | 14 | 2,633,586 | 2,726,549 | 330,955 | 165,477 |
|  | 15 | 2,304,185 |  |  |  |
|  | 16 | 3,050,468 |  |  |  |
|  | 17 | 2,917,959 |  |  |  |
| 6 hr | 18 | 3,377,770 | 2,867,943 | 1,058,960 | 529,480 |
|  | 19 | 3,439,098 |  |  |  |
|  | 20 | 1,280,125 |  |  |  |
|  | 21 | 3,374,781 |  |  |  |
| 24 hr | 22 | 653,548 | 841,889 | 215,407 | 124,366 |
|  | 23 | 795,359 |  |  |  |
|  | 24 | 1,076,761 |  |  |  |

Figure 3:
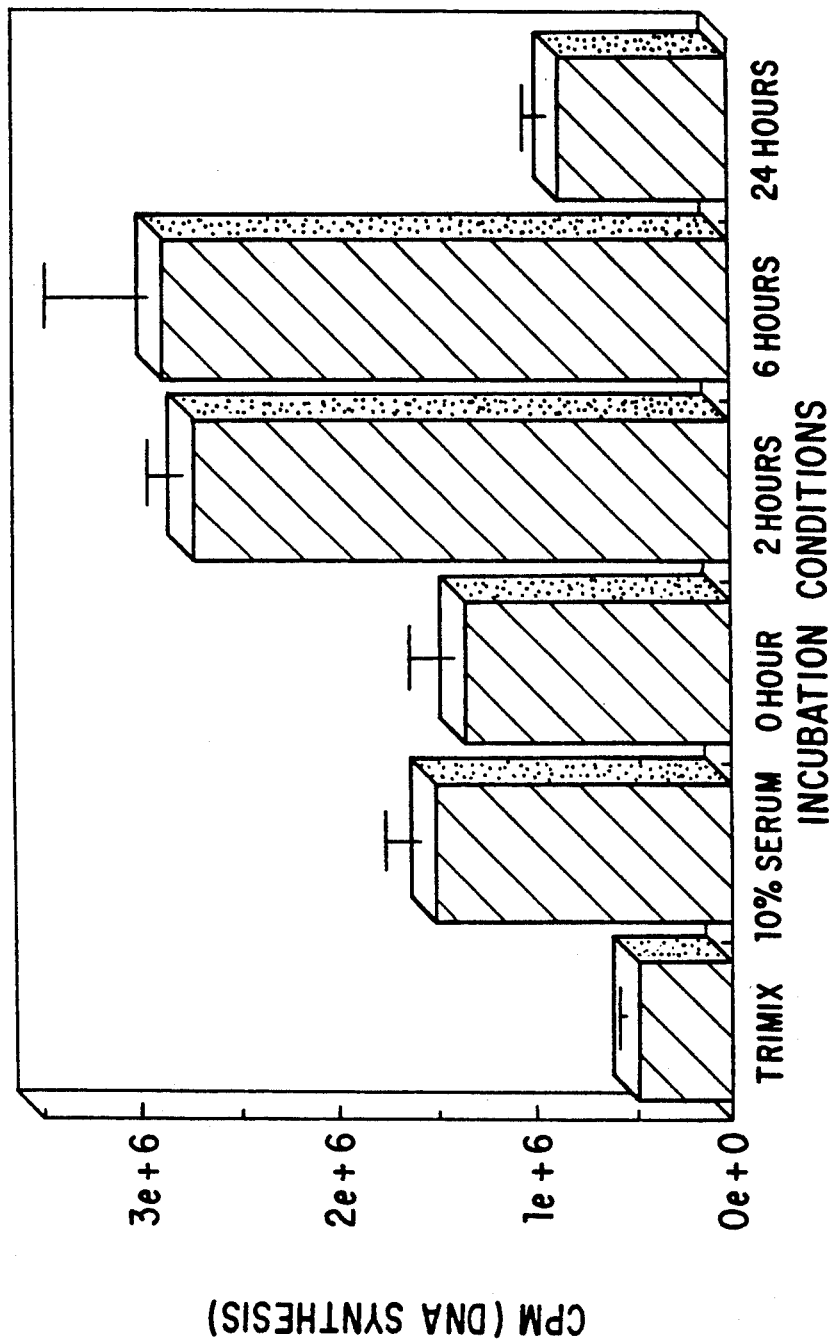
FIG. 3 shows the effects of cat anterior chamber fluid on DNA synthesis by BCEC.

Calculating the means and standard error of the means for each test condition, it is apparent that there was substantial stimulation of DNA synthesis by the anterior chamber fluid samples. The results are shown graphically in FIG. 3. The relative fold stimulation for each of the conditions relative to CDM are shown in Table 4.

TABLE 4

Relative Fold Stimulation of DNA Synthesis Compared to TRIMIX

| Sample | Fold Stimulation |
| --- | --- |
| 10% CS | 3.13 |
| 0 hr | 2.83 |
| 2 hr | 5.74 |
| 6 hr | 6.04 |
| 24 hr | 1.77 |

The statistical comparison using independent T-tests for each of the conditions are shown in Table 5 and indicates that all of the conditions are significantly different at a high level of confidence with the exception of 10% serum compared to the 0 hour samples, the 0 hour samples compared to the 24 hours samples and the 2 hours samples compared to the 6 hours samples.

TABLE 5

Statistical Analysis of BCEC DNA Stimulation By Anterior Chamber Samples

| Sample | t | p | df | Significant Difference |
| --- | --- | --- | --- | --- |
| CDM vs 10% | −5.613 | $8.04 \times 10^{-4}$ | 7 | yes |
| CDM vs 0 hr | −4.444 | $2.99 \times 10^{-3}$ | 7 | yes |
| CDM vs. 2 hr | −15.175 | $1.298 \times 1.^{-6}$ | 7 | yes |
| CDM vs. 6 hr | −2.398 | 0.047 | 7 | yes |
| CDM vs 24 hr | −3.768 | 0.0093 | 7 | yes |
| 10% vs 9 hr | 0.477 | 0.644 | 6 | no |
| 10% vs 2 hr | −4.738 | $3.195 \times 10^{-3}$ | 6 | yes |

TABLE 5-continued

Statistical Analysis of BCEC DNA Stimulation By Anterior Chamber Samples

| Sample | t | p | df | Significant Difference |
| --- | --- | --- | --- | --- |
| 10% vs 6 hr | −2.435 | 0.050 | 6 | yes |
| 10% vs 24 hr | 2.47 | 0.016 | 5 | yes |
| 0 hrs vs 2 hr | −5.018 | $2.408 \times 10^{-3}$ | 6 | yes |
| 0 hrs vs 6 hr | −2.656 | 0.037 | 6 | yes |
| 0 hrs vs 24 hr | 1.791 | 0.133 | 5 | no |
| 2 hrs vs 6 hr | −0.254 | 0.807 | 6 | no |
| 2 hr vs 24 hr | 8.499 | $3.705 \times 10^{-4}$ | 5 | yes |
| 6 hr vs 24 hr | 3.190 | 0.024 | 5 | yes |

These results demonstrate that anterior chamber fluid from cats following touch injury to the corneal endothelium contain significant levels of factors which stimulate DNA synthesis in BCEC maintained in serum free medium. In addition, the pattern of DNA synthesis levels closely parallels the RIA levels of TFG-α. The fold increase relative to serum free medium is quite substantial, reaching levels of 6 fold higher than serum free conditions. In addition, the level of DNA synthesis at 2 hours and 6 hours is higher by approximately 2 fold than the level of DNA synthesis stimulated by 10% calf serum, generally considered to be a very potent growth stimulating supplement. These results, together with RIA results, strongly indicate that TGF-α is a major component of the growth stimulating material present in anterior chamber fluids following touch injury to the corneal endothelium.

EXAMPLE 3

Inhibition of Mitotic Activity of Anterior Chamber Fluid by Antibody to TGF-α

The results of Examples 1 and 2 demonstrate that immunoreactive TGF-α material increased in anterior chamber samples after injury and that mitotic activity for BCEC also increased. The following experiment was performed to determine if the mitotic activity in anterior chamber samples could be reduced by a neutralizing antibody specific for TGF-α. The target cells chosen for the experiment were the same as for the previous experiment, early passage cultures of BCEC. The TGF-α neutralizing antibody was from Oncogene Science, Inc., and was specific for TGF-α. One-half maximum neutralization occurs at 1 μg of antibody per 0.5 ng of TGF-α.

Cultures of BCEC were seeded at approximately 50% confluence into 24 well culture plates as described above and cultured for 48 hours in CDM supplemented with 10% fetal calf serum. The cells were washed with CDM for 24 hours to synchronize the cells by serum deprivation. After the serum free medium was removed, each well received 200 μl of CDM containing 5 μCi of tritiated thymidine per well and 200 μl of test condition. Six test conditions were evaluated and each test condition contained four replicate wells for a total of 24 assay wells. The test conditions were 0% calf serum, 10% calf serum, 6 hour sample of anterior chamber fluid, TGF-a antibody, and 6 hour sample plus TGF-α antibody. Prior to addition to the assay, the antibody plus anterior chamber sample was prepared by incubating equal volumes of the antibody solution (100 μg/ml) with the 6 hour sample for 4 hours at 4° C. The cells were incubated for 48 hours, then the incubation medium was removed by aspiration and the plates submerged in 10% trichloroacetic acid and then washed in methanol. Cells and DNA were solubilized in 1 ml of 0.1N NaOH and 900 μl of the solution were added to a scintillation cocktail and the radioactivity measured with a beta scintillation counter.

Figure 4:
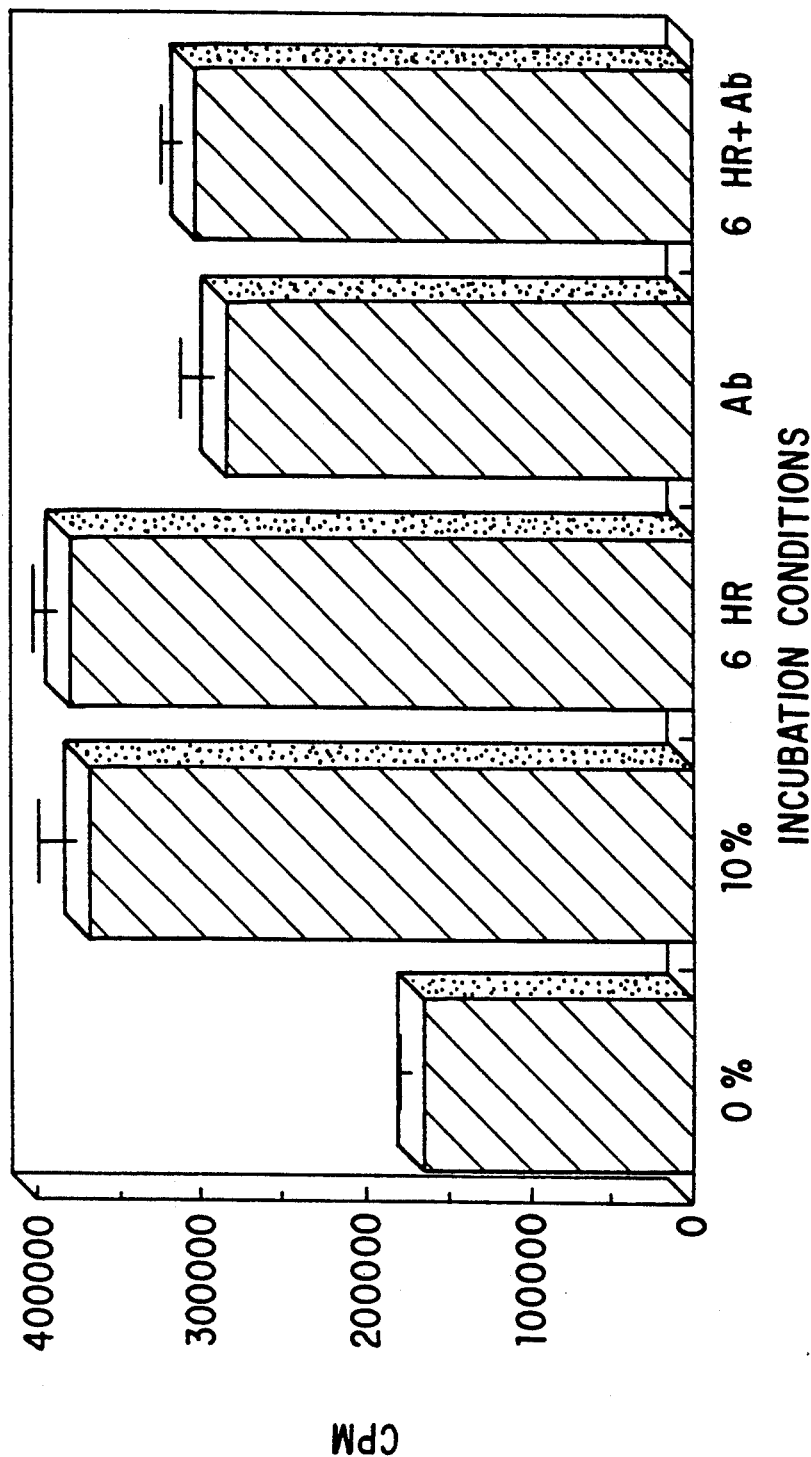
FIG. 4 is a graph showing the effect of TGF-α antibody on DNA synthesis of BCEC incubated with anterior chamber fluid samples.

The results of the assay are shown in FIG. 4. The mean incorporation of tritiated thymidine for the 6 hour anterior chamber sample was significantly higher ($p < 0.05$) than the level of DNA synthesis measured when the TGF-$\alpha$ neutralizing antibody was added to the 6 hour sample. The 20% decrease in mitotic activity caused by adding the TGF-$\alpha$ antibody to the 6 hour anterior chamber sample was not due to a nonspecific toxic effect of the antibody for when the TGF-$\alpha$ antibody was added to the CDM alone it caused a small but significant increase in DNA synthesis by the BCEC. Thus, at least 20% of the mitotic activity in the anterior chamber samples could be attributed to TGF-$\alpha$ activity. Furthermore, the percent reduction of DNA synthesis by the antibody may underestimate the actual stimulation contributed by TGF-$\alpha$ since some dissociation of the antibody-TGF-$\alpha$ complex may occur during the culture period at 37° C. due to the experimental design which required that the TGF-$\alpha$ antibody be added during the culture period.

EXAMPLE 4

Stimulation of BCEC DNA Synthesis by TGF-$\alpha$

The previous examples demonstrated that immunoreactive TGF-$\alpha$ was present in anterior chamber fluid of cats following touch injuries to the endothelium and that at least 20% of the mitotic activity of the anterior chamber samples was inhibited by a neutralizing antibody specific for TGF-$\alpha$. The following experiment was performed to determine the relative potency of TGF-$\alpha$ as a mitogen of BCEC in culture.

Pure cultures of BCEC were established from freshly obtained cow eyes by trypsin treatment of the endothelial surface. Early passage cultures were trypsinized and seeded into 24 well plates as described above. After the cells had been synchronized by serum deprivation, BCEC were cultured in CDM containing tritiated thymidine and solutions of peptide growth factors produced by recombinant DNA technology. Radioactivity incorporated into DNA was measured as described previously.

As shown in FIG. 5, the ten peptide growth factors tested could be grouped into three groups based upon their relative ability to stimulate DNA synthesis of cultures of BCEC. TGF-$\alpha$ was a very potent mitogen for BCEC in the absence of other added serum components, second only to EGF in potency. TGF-$\alpha$ at the three levels tested (0.2 nM, 2 NM and 20 nM) stimulated a nearly linear increase in DNA synthesis from 250% to 300% above the level of serum-free CDM. Other peptide growth factors, including insulin, vaccinia growth factor, and transforming growth factor beta, all stimulated moderate increases in DNA synthesis (130%–200%) compared to CDM, while several growth factors, including platelet-derived growth factor, nerve growth factor and multiplication stimulating activity failed to stimulate DNA synthesis of BCEC. These results demonstrate that only a few peptide growth factors, including TGF-$\alpha$ are capable of stimulating extensive levels of DNA synthesis of a BCEC in the absence of other serum components.

EXAMPLE 5

Administration of a Viscoelastic Composition Comprising TGF-$\alpha$ During Cataract Surgery It is well-known to administer viscoelastic compositions to the anterior chamber of the eye during cataract surgery. Typically, the viscoelastic composition is placed into the anterior chamber promptly following the incision to maintain the shape of the chamber during the surgical procedure. In accordance with the present invention, conventional procedures known to persons skilled in the art are followed with the exception that the viscoelastic composition contains TGF-$\alpha$ to enhance the healing of the corneal endothelium following the surgery.

An incision is made and Healon TM (sodium hyaluronate, 1.0%, from Pharmacia) containing 100 μg/ml TGF-$\alpha$ is administered to the anterior chamber. The solution was made by aseptically mixing the Healon TM with a concentrated solution of TGF-$\alpha$ in saline. The lens capsule then is opened and the lens is removed either via expression of the lens or by phacoemulsification in accordance with conventional procedures. The posterior capsule commonly is left intact to hold the intraocular lens. The capsule can be filled with the same viscoelastic composition to aid in the lens insertion. The composition also can be used to coat the lens prior to insertion to protect the ocular tissues from possible touches to the lens.

The majority of the Healon TM containing the TGF-$\alpha$ is removed at the conclusion of the surgery to minimize post-surgical intra-ocular pressure rise. The eye then is closed and the surgical procedure completed.

In an alternative embodiment, after the majority of the Healon TM is removed, an irrigating solution, such as BSS Plus, to which TGF-$\alpha$ has been added at a concentration of 100 μg/ml is used to refill the anterior chamber of the eye before the incision is closed.

EXAMPLE 6

Administration of TGF-$\alpha$ in an Injectable Formulation

A patient is diagnosed as requiring a corneal implant due to endothelium failure as a result of such conditions as Fuch's dystrophy or a marginal endothelial count either prior to or after cataract surgery. As an alternative to transplant surgery, the patient undergoes a single or series of intraocular injections of a solution of TGF-$\alpha$ in buffered saline. The concentration of the TFG-$\alpha$ is 100 μg/ml and 0.1 ml of solution are injected into the anterior chamber per injection. The injections enhance endothelial cell division.

I claim:

1. A method for treating corneal endothelial wounds of a warm-blooded animal in need of the treatment which comprises administering into the anterior chamber of the eye of said animal and in contact with the corneal endothelium an ophthalmic composition in an amount effective to promote healing of the corneal wound comprising TFG-$\alpha$ in a viscoelastic carrier.

2. A method in accordance with claim 1, wherein the wound is a result of a surgical procedure and the TGF-$\alpha$ is administered during or at the conclusion of the surgery.

3. The method of claim 1, wherein the ophthalmic composition comprises hyaluronic acid, collagen, chondroitin sulfate, polyacrylamide or hydroxypropylmethylcellulose.

4. The method of claim 1, wherein the ophthalmic composition comprises from about 1 μg/ml to about 100 μg/ml TFG-α.

5. The method of claim 4, wherein the ophthalmic composition comprises from about 30 μg/ml to about 100 μg/ml TFG-α.

6. The method of claim 5 wherein about 50 μg TFG-α is administered to the anterior chamber.

7. The method of claim 1, wherein said administering step is carried out prior to or during an intra-ocular lens implantation procedure.

* * * * *